United States Patent [19]

Tayot et al.

[11] Patent Number: 5,234,991
[45] Date of Patent: Aug. 10, 1993

[54] POROUS MINERAL SUPPORT COATED WITH AN AMINATED POLYSACCHARIDE POLYMER

[75] Inventors: Jean-Louis Tayot, la Tour de Salvagny; Michel Tardy, Lyons, both of France

[73] Assignee: Pasteur Merieux Serums and Vaccines, Lyons, France

[21] Appl. No.: 26,856

[22] Filed: Mar. 17, 1987

Related U.S. Application Data

[60] Division of Ser. No. 714,525, Mar. 21, 1985, Pat. No. 4,673,734, which is a continuation of Ser. No. 238,957, Feb. 27, 1981, abandoned, which is a continuation of Ser. No. 708,632, Jul. 26, 1976, abandoned.

[30] Foreign Application Priority Data

Jul. 29, 1975 [LU] Luxembourg ............... 73094

[51] Int. Cl.⁵ ............... C08G 63/48; C08G 63/91; B01D 39/00; B01D 39/02
[52] U.S. Cl. ............... 525/54.1; 210/502.1; 210/503; 210/509; 210/635; 210/656; 435/176; 435/178; 435/181; 514/59; 530/364; 530/417
[58] Field of Search ............... 525/54.1; 502/7, 62, 502/401, 404; 514/59; 536/51; 530/364, 417, 830; 210/503, 509, 502.1, 635, 656, 927; 55/67, 386; 435/176, 178, 181

[56] References Cited

U.S. PATENT DOCUMENTS

| | | | |
|---|---|---|---|
| 3,352,424 | 11/1967 | Guebert et al. | 502/62 |
| 3,851,057 | 11/1974 | Kuzuya | 514/59 |
| 4,335,017 | 5/1982 | Miles | 502/7 |
| 4,336,161 | 6/1982 | Rosevear et al. | 502/7 |

*Primary Examiner*—Nathan M. Nutter
*Attorney, Agent, or Firm*—Cushman, Darby & Cushman

[57] ABSTRACT

A porous mineral support such as a porous mineral oxide coated with an aminated polysaccharide polymer has cationic characteristics and is capable of reversibly fixing thereto biological macromolecules. This material is employed in the separation and purification of said biologic macromolecules.

27 Claims, No Drawings

POROUS MINERAL SUPPORT COATED WITH AN AMINATED POLYSACCHARIDE POLYMER

This is a division of application Ser. No. 06/714,525, filed Mar. 21, 1985, and now U.S. Pat. No. 4,673,734 which is a continuation of Ser. No. 06/238,957 filed Feb. 27, 1981, and now abandoned which is a continuation of Ser. No. 05/708,632 filed Jul. 26, 1976, now abandoned.

The present invention relates to new material having a cationic character which is capable of reversibly fixing thereto biologic macromolecules, such as various proteins, nucleic acids and the like.

Until now, it was not possible to produce ion exchange chromatography supports for such types of molecules which supports exhibited both excellent chemical properties and excellent mechanical characteristics.

While numerous supports have been proposed which exhibit very good chemical properties, thus permitting selective separations, generally these supports possess quite inferior mechanical properties.

On the other hand, supports having very good mechanical properties have also been proposed principally for preparative or industrial use in ion exchange columns. However, it has been found that these supports possess quite insufficient chemical properties, especially with regard to biologic macromolecules since these supports exhibit irreversible absorption sites.

The present invention overcomes the above noted deficiencies and provides a support which can ideally be employed in modern separation techniques involving biologic macromolecules, these techniques requiring the use of a support exhibiting both excellent chemical activity and great mechanical resistance.

Thus, the present invention relates to a new material which is capable of reversibly fixing biologic macromolecules, this material comprising a mineral support, such as a porous mineral oxide, coated directly on the surface thereof with an aminated polysaccharide polymer.

It has now been found that this type of material enhances the mechanical, physical, chemical and biologic qualities of the porous mineral support while, at the same time, providing a novel chemical surface which is particularly suitable for chromatographic separation of biologic macromolecules.

In accordance with the present invention, the porous mineral support can be silica, alumina, magnesia, an oxide of titanium, or their natural or synthetic derivatives, such as glass, silicates, kaolin or the like.

The aminated polysaccharide polymer can be coated onto surface of the porous mineral support by a sizing technique. This adhesion mechanism does not appear to be only of the electrostatic type because porous supports, such as alumina which has a non-negative surface, can also be coated with aminated polysaccharide polymer so as to provide materials, according to the present invention, having excellent qualities.

Therefore, the coating of aminated polysaccharide polymer is adhered to the support in an essentially irreversible manner. However, under certain conditions, which are described below, it is possible, after a certain time of use, to regenerate the porous mineral support which can then again be re-impregnated or coated with an aminated polysaccharide polymer.

The porous mineral support must have a well defined, controlled porosity. The internal surface of the support must be lower than or equal to 100 m$^2$/g and, preferably, between 5 and 80 m$^2$/g. The average pore diameter must be greater than or equal to 25 millimicrons and, preferably, between 50 and 1000 millimicrons, although other values can be employed, depending upon the ultimate use envisaged. For the greatest internal surface or the smallest pore diameters, the internal surface of the support becomes inaccessible to the aminated polysaccharide polymer and subsequently to the macromolecules to be separate. In accordance with a preferred embodiment of the present invention, the porous mineral support is silica or alumina and, preferably, a porous silica support having anionic characteristics obtained, for example, in accordance with the processes described in French Patent Nos. 1,473,239; 1,473,240; 1,475,929 and 1,482,867. Commercially available porous silicas can be employed. Representative commercial silicas include those available under the names Spherosils X0B 030; X0B 015 and X0C 005 sold by Rhone-Poulenc Chemie Fine. These silicas have internal surface areas of, respectively, 50, 25 and 10 m$^2$/g.

The aminated polysaccharide polymer which is employed to impregnate and to cover the internal surface of the porous mineral support must have a pronounced cationic character and must have good hydrophilic properties. It also must have a molecular weight at least equal to 10$^4$ Daltons, preferably between 10$^5$ and 10$^6$ Daltons. Generally, any aminated polysaccharide polymer meeting these criteria can be employed. Particularly useful polymers of this type are the aminated derivatives of dextran, starch, cellulose, agarose or natural or synthetic polymers of known monosaccharides, provided that they do not include anionic groups, such as carboxylic or sulfonic groups in an appreciable amount so that the polymer possesses significant electric charges which would impede the use of the support as an anion exchanger.

The amine functions of the polysaccharide polymer can be primary, secondary, tertiary or, optionally, quaternary. Secondary, tertiary and quaternary functions are, however, preferred.

According to a preferred embodiment, the aminated polysaccharide polymer has the formula:

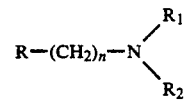

wherein

R represents the residue dextran, starch, cellulose or agarose, n is a whole number from 1 and 10 and, preferably, from 2 and 5, and R$_1$ and R$_2$ each independently represent —CH$_3$, —CH$_2$—CH$_3$, —CH$_2$OH, —CH$_2$—CH$_2$OH or —CH$_2$—CHOH—CH$_3$. This compound can also be quaternized with a conventional quaternizing agent, such as alkyl or hydroxy alkyl halides, particularly the iodides and bromides thereof or dimethyl sulfate and the like.

Representative compounds of this type include, in particular, those available under the names of DEAE DEXTRAN (diethylaminoethyl dextran) having a molecular weight of 500,000; QAE DEXTRAN (quaternized diethylaminoethyl dextran) sold by Pharmacia;

DEAE starch (diethylaminoethyl starch), as well as cationic starches, such as those commercially available under the name CATO by Societe Roquette National.

According to another preferred embodiment of the present invention, the aminated polysaccharide polymer can be crosslinked with a crosslinking agent, such as 1,4-butanediol diglycidyl ether, epichlorohydrin, epibromohydrin or a diepoxide of the formula

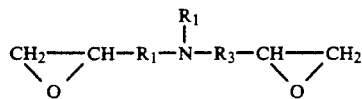

wherein $R_1$ is alkyl having 1-20 carbon atoms, preferably a lower alkyl having 1 to 4 carbon atoms, and $R_2$ and $R_3$ represent a hydrocarbon chain having 1 to 10 carbon atoms and preferably a lower alkylene having 1 to 4 carbon atoms. A representative diepoxide is one having the formula

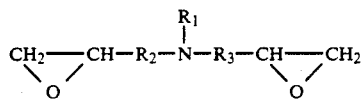

The present invention also relates to a process for preparing the material of the present invention having cationic characteristics which is capable of reversibly fixing biologic macromolecules thereto.

This process can be carried out in accordance with two different methods, i.e., column impregnation and oven impregnation.

In accordance with the first method, the porous mineral oxide is introduced into a chromatographic column by directly pouring into the column the dry, homogeneous powder, washing and homogenizing the same to expel air bubbles by passing therethrough a solution of an acid, for example, 0.1N HCl and then passing therethrough a buffer of pH 3 to 12 (for example, 0.05M Tris (hydroxymethyl) aminomethane (TRIS)-pH 7) until equilibrium is achieved.

Then the animated polysaccharide polymer as a hot or cold solution in the aforementioned buffer or in water, adjusted to the same pH is introduced into the column. Excess aminated polysaccharide polymer is removed by eluting initially with the preceding buffer and then with a salt solution, for example, a solution of trisodium citrate; the absence in the final eluate of aminated polysaccharide polymer can be determined by electrophoresis in cellulose acetate and coloration of a plate culture to poppy red, or by precipitation in the presence of a polyacrylic acid.

The material thus obtained provided reversible fixation in an amount of about 20-50 mg of protein per gram of support.

This material exhibits great stability over a wide pH range, i.e., from about 3 to 12.

According to the second method, i.e., oven impregnation, the porous mineral oxide after having been weighed is impregnated, cold or hot, with an aqueous solution of the aminated polysaccharide polymer, at a pH ranging indifferently from 3 to 12. The thus impregnated porous support is oven dried at a temperature between 50° and 120° C., preferably at 80° C., until a constant weight is obtained.

The resulting powder is then homogenized and screened, if necessary, to remove any agglomerates. The material obtained by oven impregnation can be employed in a column after previously washing it with an 0.05M-pH 4 or an 0.05M-pH 6.8 buffer or citrate solution. The material obtained by this method provides reversible fixation in an amount of about 40 to 200 mg of protein per gram of support.

As will be appreciated, the oven impregnation method significantly improves the protein fixation capacity of the support.

The oven impregnation method also provides a coating of aminated polysaccharide polymer which is practically irreversibly adhered to the porous metal oxide substrate. In effect, this oven impregnated material can be washed with 0.1N HCl, or with 0.1N NaOH or with 0.1N ammonia without adversely affecting its anion exchange properties. On the other hand, a column impregnated support subjected to essentially the same washing treatment undergoes regeneration to the initial porous mineral oxide. If it is desired to regenerate the oven-impregnated porous mineral oxide, it is necessary to treat the material under much more energetic conditions, such as, for example, treating it with fuming nitric acid.

Thus, the oven-impregnation method provides a material of the present invention which can be employed in numerous operations without adversely affecting its excellent anion exchange characteristics.

According to another embodiment of carrying out the process of the present invention, it is possible, after either of the above-described impregnation procedures and after having dried the thus impregnated support in a oven at a temperature between about 50° and 80° C. so as to obtain a homogeneous powder, to treat the resulting product with a solution of a crosslinking agent in a volatile solvent, such as ethyl ether. Any of the aforementioned crosslinking agents can be employed.

In this embodiment, the product being treated is agitated until the solvent has completely evaporated so as to achieve uniform impregnation with the crosslinking agent. The thus treated support is then heated to a temperature between 40° and 120° C., preferably near 80° C., for about 15 hours. After optionally screening the support, the same is introduced dry into a column, washed initially with NaOH, then with a sodium chloride solution and finally equilibrated with a desired chromatography buffer.

This crosslinking operation provides a material exhibiting excellent qualities which can be washed in a regular fashion by 0.1N NaOH or ammonia or even 0.1N HCl without altering either its separation qualities or its capability for reversibly fixing proteins.

The capacity of the crosslinked material is between 40 and 200 mg of protein per gram of support. For surfaces of the initial porous support ranging from 10 to 80 $m^2/g$, this capacity is nearly constant.

As for the column-impregnated or oven-impregnated material, it is also possible to wash the material with concentrated nitric acid so as to regenerate the porous mineral oxide support or substrate.

The present invention also relates to the use of the new materials described above in the purification or the separation of biologic macromolecules, preferably proteins.

Generally, this use comprises employing the cationic properties of the material made in accordance with the present invention either to selectively fix the biologic macromolecules that one desires to isolate or purify, or to selectively retain the non-desired impurities or other proteins.

Selective fixation of proteins is easily achieved by regulating the pH and the molarity according to methods well known in the use of ion exchangers.

Generally, this use comprises passing a solution containing the biologic macromolecules that are desired to be isolated or purified over a support of the present invention, the pH and the molarity of the solution being regulated so that the support selectively fixes either the biologic macromolecules desired to be purified or isolated or the non-desired impurities.

In the situation where the macromolecules that are desired to be purified or isolated, are fixed thereon, they are subsequently eluted with a solution of suitable pH and molarity.

In the situation where the impurities are fixed on the support of this invention, the biologic macromolecules in solution are recovered directly. Thereafter, the impurities are eliminated by eluting with a solution of suitable pH and molarity whereby the coating material is regenerated for further use.

Representative applications for using the coated support of the present invention include:

(a) purification of gamma globulins found in human or animal serums or plasmas;

(b) elimination of hemoglobin in the process of purifying albumin starting with placental blood and concentration of other proteins;

(c) concentration of a protein solution diluted with an alcoholic medium and the elimination of the alcohol;

(d) concentration and purification of albumin in a sodium caprylate solution; and (e) concentration and purification of gangliosides found in aqueous extracts of animal brains.

These different applications of the material of the present invention are described in detail in the examples given hereafter.

The material, according to the present invention, also can be employed in the purification of antibodies or antigens. In this case, the antigens or antibodies are fixed on the material which is then employed for the purification and the concentration of the corresponding antibodies and antigens.

Thus, it is possible to immobilize or fix (1) albumin, alpha, beta and gamma globulins, human or animal; and (2) all bacterial and viral antigens provided they possess negative electric charges at pH 6.8, which is the case, for the most part, of known proteins, polysaccharides and nucleic acids.

Further, the following can also be immobilized or fixed on the coated substrate of the present invention: bacterial toxins, tetanic anatoxins, $HB_s$ antigen associated with hepatitis B, grippal virus, rabies virus, herpes virus, measles virus, rubella virus, adenovirus, papovavirus, arbovirus, rhinovirus, picornavirus, enterovirus, poxvirus, myxovirus, paranyxovirus, reovirus, coronavirus or the degradation products, such as their various antigens.

Just as the materials, according to the present invention, can immobilize or fix antigens or antibodies, they can also immobilize various enzymes leading to the following materials of enzymatic activity: pepsin, trypsin, chrymotrypsin, plasmin, lacticodeshydrogenase, L aminoacylase, invertase, glucose isomerase, amyloglucosidase, glucose oxydase, catalase, lipase and urease.

According to a particular embodiment, these immobilized macromolecular substances can be irreversibly fixed if they are subsequently crosslinked with a crosslinking agent, such as enumerated above. This crosslinking operation is in general carried out at ambient temperature.

Finally, the material, according to the present invention, can also be used to immobilize molecules of weak molecular weight substances, such as certain amino acids or certain ligands possessing amine functions, alcohols or thiols in the presence of a coupling agent, for instance, glutaraldehyde or a diepoxy compound, such as defined above.

Thus, it is possible to immobilize, for example, lysine and the resulting material can be used to purify or eliminate plasminogen or plasmin protein of blood having a strong affinity for lysine.

It is also possible to immobilize various steroids and to use such materials thus modified to purify their transfer proteins. Finally, it is possible to immobilize various cellular receivers, for example, gangliosides previously deacetylated to render the aminated functions thereof the most reactive and to use these materials for the removal, the neutralization or the purification of their ligands.

The following examples are given to illustrate the invention. Unless otherwise specified, all parts and percentages are by weight.

EXAMPLE 1

10 g of Spherosil X0C 005 are directly poured into a chromatographic column in the form of a dry and homogeneous powder. 100 ml of an 0.1N HCl solution are then introduced into the column using a peristaltic pump at a flow rate of 500 ml/hr so as to wash and impregnate the column and to expel all air bubbles. Preferably ascending elution is preferred. A buffer having a pH 3 to 12, for example, 0.005M TRIS buffer at pH 7, is then introduced into the column until equilibrium, controlled by measurement of the pH and the resistivity of the buffer from leaving the column, is achieved. About 150 ml of a 1% solution of DEAE Dextran (or 30 ml of a 5% solution) in the aforementioned buffer or in water adjusted to this pH are then introduced at a flow rate of 100 ml/hr. Finally, excess DEAE Dextran not fixed on the column is eluted initially by the said buffer and then by 0.05M, pH 4 citrate and by 0.05M, pH 8 citrate, at a flow rate of 1000 ml/hr. Finally, the column is equilibrated with the desired chromatography buffer. The absence of DEAE Dextran in the final eluate can be determined by electrophoresis in cellulose acetate and coloration of plate culture poppy red, or by precipitation in the presence of polyacrylic acid. The thus impregnated support is stable over a wide pH range, i.e., about 3 to about 12 and behaves as an anion exchanger. It is particularly useful in the purification or the concentration of proteins. In a suitable buffer system, it is capable of reversibly fixing 20 to 50 mg of protein per gram of impregnated support.

In this example, DEAE Dextran can advantageously be replaced by QAE Dextran.

EXAMPLE 2

10 g of Spherosil X0B 015 are weighed and impregnated with 20 ml of an aqueous solution of aminated polysaccharide, DEAE Dextran, for example, at a concentration between 1 and 10%, preferably between 5 and 8%, and at a pH indifferently between 3 and 12.

The thus impregnated support is oven dried at a temperature between 50° and 120° C., preferably at 80° C., for the time required, 15 hours, for example, to achieve a constant weight (removal of water). The resulting powder is homogenized and screened, if necessary, to remove any agglomerates, then introduced into the chromatography column.

After filling the column and previously washing with an 0.1N HCl buffer, or 0.05M-pH 4 citrate buffer, or an 0.05M-pH 6.8 citrate buffer, or 0.1N NaOH, the column is equilibrated with a buffer suitable for the type of chromatography desired.

The protein fixation capacity of the material is significantly increased to a value in the order of 40 to 200 mg/g, depending, of course, on the particular chromatographic conditions employed.

In this example, DEAE Dextran can advantageously be replaced by another aminated polysaccharide polymer, such as DEAE starch.

EXAMPLE 3

To 10 g of Spherosil X0B 030, impregnated in accordance with one of the two preceding methods with a solution of aminated polysaccharide having a pH between 8 and 13, but preferably equal to 11.5 and then oven dried to obtain a homogeneous powder, there are added 20 ml of an 0.02 to 2%, preferably an 0.15% solution of 1,4-butanediol diglycidyl ether in ethyl ether. The resulting mixture is agitated uninterruptedly at a temperature of 40° C. until complete evaporation of the ethyl ether occurs so as to obtain uniform impregnation by this diepoxy compound which serves as a cross-linking agent.

The whole is then brought to a temperature between 40° and 120° C., preferably near 80° C., for about 15 hours. After a final screening, the support is then introduced dry into the column, washed initially with 1 liter of 0.1N NaOH, then with 1 liter of molar NaCl and finally equilibrated with the chromatography buffer.

The protein fixation capacity of the material is between 40 and 200 mg per gram of support, depending on the chromatographic conditions employed. For surfaces of the initial porous support ranging from 10 to 80 $m^2/g$, this capacity is practically constant.

EXAMPLE 4

Direct purification of gamma globulins from human or animal serums or plasmas.

The following sequence of operations using 50 g of support prepared according to preceding Examples 1, 2 or 3 is employed.

The column containing said support is equilibrated at pH 6.8, although any pH ranging between 6.3 and 8 can be selected, with an 0.01-0.02M $PO_4$ buffer or an 0.05M TRIS HCl buffer or with 1 to 3 g/l NaCl, at a flow rate of 200 ml/cm$^2$/hr.

50 ml of plasma or serum, previously dialyzed against the chromatography buffer and filtered to remove any possible agglomerates are introduced into the column at an average flow rate of 50 to 100 ml/cm$^2$/hr. When using a support prepared in accordance with Example 1, the quantity of serum or plasma per sequence must be reduced to 25 ml.

The column is then washed with the chromatography buffer.

At the peak of the outflow of the column, pure gamma globulins, in immunoelectrophoresis, is collected for a yield between 50 and 100% depending upon the buffer used. While the yield is better for a pH lower than 6.8 or the strongest ionic forces, often the purity of the gamma globulins is not as good. Such a preparation of gamma globulins is free of pyrogenic substances and of antigens associated with hepatitis B (Ag HBs) which optionally is present in the crude starting material.

The other proteins retained on the column are then eluted by any buffer having a pH 4 or by the chromatography buffer to which have been added 10 to 60 g of NaCl, or finally by a 0.05M citrate buffer having a pH 4 to 8.

The duration of this sequence is about 2 hours and a new sequence can be immediately undertaken so that with a sufficiently simple automatic mechanism, about ten sequences can be carried out in the same day, which amounts to a treatment rate close to 10 liters of serum or plasma per kilogram of porous mineral oxide per day.

EXAMPLE 5

Removal of hemoglobin in the process of purifying albumin from placental blood and concentration of other proteins.

The alcohol fractionation of placental blood, according to the Cohn method, involves precipitation of globulin mass at pH 6.8 with 20 to 25% ethanol. Under these conditions, the albumin, certain alpha 1 and alpha 2 globulins and hemoglobin essentially remain in solution in the supernatant. The supernatant can be recovered by centrifuging cold, the supernatant having been diluted with an equal volume of distilled water so as to reduce the alcohol concentration, adjusted to a pH between 6 and 7 and clarified by filtering on cellulose ester membranes.

The following sequence of operations using 50 g of support prepared according to Examples 2 or 3 is employed. 100 g of support are necessary if it has been obtained in accordance with Example 1.

The column is equilibrated with an 0.01M $PO_4$ buffer or an 0.05M TRIS-HCl-pH 6 to 7, preferably 6.5, buffer at a flow rate of 200 ml/m$^2$/hr.

1000 ml of the above-described supernatant is introduced into the column at an average flow rate of 100 ml/cm$^2$/hr.

The column is then washed with the chromatography buffer at the same flow rate. The purified hemoglobin leaves the column with a negligible dilution factor, whereas the other proteins, including albumin, remain fixed on the column.

The proteins fixed on the column are then eluted from the column under conditions essentially identical to those set forth in Example 4. The peak of the column outflow contains the concentrated proteins and is practically free of hemoglobins.

The duration of the sequence is about 4 hours and a new sequence can be implemented immediately thereafter.

EXAMPLE 6

Concentration of a protein solution diluted by an alcoholic medium and the removal of said alcohol.

The fractionation of proteins, in accordance with the Cohn method, inevitably involves, during the various steps thereof, the redissolution of alcoholic precipitates. Thus it is preferable to dilute strongly the precipitate to reduce the concentration of residual alcohol which is troublesome. Then, there is required, on the one hand, the removal of the alcohol and, on the other hand, the concentration of the proteins present. This is generally carried out by concentration under vacuum, lyophilization or dialysis. These latter two steps are either very onerous or are a depyrogene source. Accordingly, an extremely convenient, rapid and economic process, in accordance with the present invention, can be carried out using, for example, a 2% solution of albumin containing 10% alcohol.

The following sequence of operations using 1 kg of support prepared in accordance with Examples 2 or 3 is employed. When the support is prepared in accordance with Example 1, the quantity of the required support is doubled. The duration of the sequence of steps is of the order of 4 hours.

The column containing said support is equilibrated with an 0.01M phosphate buffer at a pH 7 and at a flow rate of 200 ml/cm$^2$/hr.

The alcoholic solution of albumin adjusted to pH 7 by the addition thereto of HCl or NaOH, according to its initial pH, is then introduced into the column at an average flow rate of 100 ml/cm$^2$/hr.

It is thus possible to fix 200 g of albumin on this column, which amounts to about 10 liters of solution per sequence. If the albumin fixes badly on the column, it is only necessary to increase the dilution of the initial solution in distilled water so as to reduce the ionic force of the medium.

The column is then washed with distilled water at a flow rate of 200 ml/cm$^2$/hr and it is verified that the albumin does not leave the column but that the alcohol is removed.

The albumin is eluted from the column by using one of the following buffers: 0.1M NaCl or 0.05M citrate-pH 6.8 . Generally, a final concentration of albumin of about 10 to 20% is obtained and the elimination of the alcohol is essentially total. The yield of the operation is close to 100%. This process is applicable for any protein whose isoelectric point is lower than 6.5. For proteins whose isoelectric point is higher, the method is applicable providing the pH of the chromatography buffer is increased. Finally, it is obvious that any impurity present in these protein solutions can thus be removed providing the impurity is electrically neutral (glucides and polysaccharides) or is charged negatively in the same manner as the support (cations). In the case of negatively-charged impurities, these may compete with the negative proteins that are desired to be fixed on the support. In this case, if the affinity of the impurity for the support is weaker than that of the protein and if the solution is diluted sufficiently in water so as to obtain an ionic strength compatible with the fixation of the protein on the support, it is possible to eliminate even the anions. The following application illustrates such a separation.

EXAMPLE 7

Concentration and purification of albumin in a solution of sodium caprylate.

Some extremely interesting fractionation methods employ sodium caprylate to coagulate all the proteins, with the exception of albumin only, the latter remaining in solution in the presence of caprylate. A process, in accordance with the present invention, can be carried out using a solution containing 15 g/l of albumin and 3 g/l of caprylate.

The following sequence of operations using 1 kg of support prepared according to Examples 2 or 3 is employed. When the support is prepared in accordance with Example 1, the quantity of the required support is doubled.

The column containing said support is equilibrated with an 0.01M phosphate buffer at pH 6 and at a flow rate 200 ml/cm$^2$/hr.

The above albumin containing caprylate solution, adjusted to pH 6, is introduced into the column at an average flow rate of 100 ml/cm$^2$/hr. This solution can be further diluted with water if the ionic forces are too high.

About 8 l of the solution are introduced into the column. It is easy to note the fixation and to observe the continued departure of the sodium caprylate due to the very marked goat order.

The column is then washed in the chromatography buffer until no more caprylate leaves the column.

The albumin is eluted from the column in accordance with essentially the same method as in the preceding examples. A 10–20% solution of albumin is obtained which, reduced to 20%, contains less than 2.5 g/l of sodium caprylate. The total duration of the sequence is about 4 hours.

It is obvious that this method can be generalized for the purification and concentration of various negatively-charged bioligic molecules, such as nucleic acids, proteins, anionic polysaccharides, anionic glycolipides at certain pH values. The following example illustrates that this generalization is possible and that such a column permits, without consequence, the passage therethrough of liquids having very diverse polarity.

EXAMPLE 8

Concentration and purification of gangliosides present in aqueous extracts of animal brains.

Gangliosides are glycolipides of which biochemists presently study the extremely important physiologic or pathologic role that they play on a level of cellular membranes, as receptor and effector. They contain, more or less, sialic acid, and at this content, are charged negatively above a pH of about 3.

Starting with 1 kg of calf brains, it is possible to obtain an aqueous extract of about 7 liters, in accordance with a process described in the publication by L. Svennerholm, "Gangliosides, Isolation," Methods in Carbohydrate Chemistry, Vol. 6, Edition R. L. Whister and J. N. Bemiller, Acid. Press, New York, 1972.

This aqueous extract is introduced directly into a column of 50 g of a support made in accordance with Example 3, which has previously been equilibrated with an 0.05M TRIS-HCl buffer at pH 6.8. The flow rate of the extract is 200 ml/cm$^2$/hr. All the gangliosides are fixed into the column under these conditions. The column is then washed with the following solutions in the order indicated:

(1) TRIS-HCl, 0.05M, pH 6.8
(2) NaOH, 0.1N
(3) H$_2$O and
(4) Chloroform-methanol-water in the following volume proportions (30-60-25), these washings removing numerous impurities.

The gangliosides in concentrated and purified form are then eluted using the following mixture: chloroform-methanol-0.1N HCl in the respective volume proportions (30-60-25) and at the same flow rate.

During elution, the peak of the column outflow which is recovered and neutralized by the addition of 0.1N NaOH, is then evaporated and taken up in any chromatographic system for analysis. The yield is 100%. It is remarkable to note that the column can, without any harmful consequences, tolerate first an organic solvent and then aqueous solution or vice-versa. This advantage can be exploited in particular purification operations or in maintaining sterile conditions in the column.

EXAMPLE 9

Use of the material, according to the present invention, as a support for tetanic anatoxin to purify and concentrate antitetanic antibodies.

The increased protein fixation capacity disclosed in the preceding applications can be put to profit to immobilize or fix tetanic anatoxin on a column of a porous mineral support. For example, 10 g of Spherosil XOC 005 (specific surface—10 m$^2$/g) are impregnated with DEAE Dextran in accordance with Example 1. The column, filled with this coated support, is equilibrated with an 0.01M phosphate buffer at pH 6.8. 25 ml of tetanic anatoxin (biologic titer near 1500 Lf or flocculating units) are diluted to 250 ml in this same buffer and uninterruptedly introduced into the column. At the beginning of the passage of the said anatoxin through the column, the fixation of the tetanic anatoxin is quantitative. No trace of the anatoxin is detectable leaving the column as measured by appropriate immunologic methods, up to about 200 ml of eluate. The last 50 ml of the anatoxin are introduced even though the support in the column has a uniform and complete coating of tetanic anatoxin. The column is then rinsed with the chromatography buffer. It is possible to immobilize definitively the tetanic anatoxin by reticulating it, so it will not be eluted over a sufficiently wide range of pH values, i.e., 2 to 12.

Reticulation is effected by uninterruptedly circulating 100 ml of an 0.5% glutaraldehyde solution in an 0.01M phosphate buffer at pH 6.8 for 2 hours at a flow rate of about 40 ml/cm$^2$/hr and at ambient temperature.

Then the column is rinsed, successively by the following buffers:

(1) 0.01M phosphate-pH 6.8
(2) 0.2M glycocoll-pH 7.2 (with and without 60 g/l NaCl)
(3) 0.05M citrate-pH 2.8 and
(4) 0.2M glycocoll at pH 7.2 for final backflow and preservative action.

The column is then ready for use and can be employed for numerous identical purification sequences. Several tens of successive sequences have thus been carried out and the coated support retains essentially all its characteristics.

The following sequence of operations using 10 g of the porous mineral support coated, as set forth above, is employed.

1.5 liters of a solution of gamma globulins or of serum or of plasma, adjusted to the following concentrations: Glycocoll 15 g/l; NaCl; pH 7.2 and titrating about 5 I.U./ml of antitetantic antibodies are introduced at ambient temperature into the column at a flow rate of 40 ml/cm$^2$/hr. Less than 5% antitetanic antibodies are detectable leaving the column as measured by appropriate immunologic methods, whereas all the other proteins pass through the column.

The column is initially rinsed with 0.2M glycocoll buffer at pH 7.2, containing 60 g/l of NaCl and then with the same buffer without NaCl until the eluate of the column no longer exhibits any significant absorption of ultraviolet light at 280 millimicrons. Each of the above buffers is introduced into the column for about 15 minutes at a flow rate of 200 ml/cm$^2$/hr.

The elution of the antitetanic antibodies fixed on the column of anatoxin is then carried out by passing through the column an 0.5M trisodium citrate-citric acid buffer having a pH 2.8, at 20° C. and at a flow rate of 40 ml/cm$^2$/hr.

The eluate of the column is collected in a refrigerated receptor and immediately neutralized to pH 7 by the uninterrupted addition of normal NaOH controlled by a pH meter recorder. As soon as the peak elution, measured by absorption at 280 millimicrons, is completed, the column is re-equilibrated with the initial glycocoll buffer, and another sequence, as defined above, can immediately be implemented. The solution of purified antitetanic antibodies can be concentrated by such conventional means as ultrafiltration or precipitation by polyethylene glycol, alcohol or ammonium sulfate. The average activity of the solutions of the antitetanic antibodies thus purified is 30 to 100 I.U./mg of protein. The yield in antitetanic antibodies varies from 20 to 100%.

By rigorously following the same procedure as that described in Example 9, it is possible to immobilize different antigens or antibodies, such as those which have been set forth in the description of the present case.

For certain antigens whose isoelectric point is greater than pH 6, it is preferable to carry out the fixation step on the column in an 0.01M phosphate buffer at pH 8, rather than pH 6.8. It is also preferable to replace the phosphate ions by chloride ions by using 0.01 or 0.05M sodium chloride at the same pH 8 level. Also, a solution which could be employed can consist of quaternary exchangers strongly ionized at pH 8. This is particularly the case involving proteins with beta 2, gamma 1 or gamma 2 type antibody activity derived from such animal species as goats, lambs, rabbits, horses or guinea pigs, or humans.

EXAMPLE 10

To 10 g of Spherosil X0B 015 impregnated with DEAE Dextran, in accordance with any one of Examples 1, 2 or 3, 30 ml of an 0.1% solution of butanediol diglycidyl ether are added. The resulting mixture is then evaporated for 30 minutes at 80° C. to remove the solvent. There is added thereto a solution of lysine in water at pH 11.5 (30 ml to 1%). The whole is then heated for 15 hours at 80° C. The resulting material is put into a column and washed with an 0.05M citrate buffer at pH 6.8. By comparison to a control support which has not been treated with any coupling agent, it was easily verified that a high percentage of lysine was coupled definitively on the support impregnated with DEAE Dextran. Colored reactions with ninhydrin are useful for such a measurement.

Using the column thus formed with material covered with lysine, it is possible to effect, with excellent results, purification or elimination from plasminogen or from plasmin, blood protein having a great affinity for lysine.

What is claimed is:

1. A particulate material comprising a plurality of discrete porous rigid support particles and a deformable xerogel retained within and substantially filling the pore structure of the support particles, said deformable xerogel being capable of sorbing chemical species from solution.

2. A particulate material comprising a plurality of discrete porous rigid support particles, and a deformable xerogel retained within and substantially filling the pore structure of the support particles, said deformable xerogel comprising an affinity chromatography agent such that the particulate material is a composite material having affinity chromatography properties.

3. A particulate material comprising a plurality of discrete porous rigid support particles and a deformable xerogel retained within the pore structure of the support particles, said deformable xerogel being capable of sorbing chemical species from solution.

4. A particulate material comprising a plurality of discrete porous rigid support particles, and a deformable xerogel retained within the pore structure of the support particles, said deformable xerogel comprising an affinity chromatography agent such that the particulate material is a composite material having affinity chromatography properties.

5. A particulate material comprising a plurality of porous material support particles impregnated with and containing a sufficient amount of an aminated polysaccharide polymer so as to permit reversibly fixing biologic macromolecules therewith.

6. A particulate material comprising a plurality of porous mineral support particles impregnated with and containing a sufficient amount of an aminated polysaccharide polymer so as to permit reversibly fixing biologic macromolecules therewith, said aminated polysaccharide polymer being affixed directly on the surface of said porous mineral support particles, said porous mineral support having an internal surface area lower than or equal to 100 m²/g and an average pore diameter equal to or greater than 25 millimicrons.

7. The particulate material of claim 6 wherein the porous mineral support is a porous mineral oxide selected from the group consisting of silica, alumina, magnesia and an oxide of titanium.

8. The particulate material of claim 6 wherein the porous mineral support has an internal surface area ranging from 5 to 80 m²/g.

9. The particulate material of claim 6 wherein the pore diameter of the porous mineral support ranges from 50 to 1000 millimicrons.

10. The particulate material of claim 6 wherein the porous mineral support is silica having an internal surface area of 10 m²/g, 25 m²/g or 50 m²/g.

11. The particulate material of claim 6 wherein the aminated polysaccharide polymer is soluble in water and has a molecular weight greater than or equal to $10^4$ Daltons.

12. The particulate material of claim 11 wherein the aminated polysaccharide polymer has a molecular weight ranging from $10^5$ to $10^6$ Daltons.

13. The particulate material of claim 6 wherein the amine function of the polysaccharide polymer is primary, secondary, tertiary or quaternary.

14. The particulate material of claim 6 wherein the aminated polysaccharide polymer is a natural or synthetic aminated derivative of dextran, cellulose, agarose or starch.

15. The particulate material of claim 6 wherein the aminated polysaccharide polymer is selected from the group consisting of (a) an aminated polysaccharide having the formula

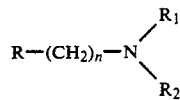

wherein
R is the residue of dextran, starch, cellulose or agarose,
n is a whole number from 1 to 10,
$R_1$ and $R_2$ each independently represent —CH₃, —CH₂—CH₃, —CH₂OH, —CH₂—CH₂OH or —CH₂—CHOH—CH₃, and (b) the aminated polysaccharide polymer of (a) quaternized with a quaternization agent selected from alkyl halide, hydroalkyl halide or dimethyl sulfate.

16. The particulate material of claim 14 wherein the aminated polysaccharide derivative is diethylaminoethyl dextran, quaternized diethylaminoethyl dextran or diethylaminoethyl starch.

17. The particulate material of claim 6 wherein the aminated polysaccharide polymer is crosslinked with a crosslinking agent selected from 1,4-butanediol diglycidyl ether, epichlorohydrin, epibromohydrin or a diepoxide of the formula

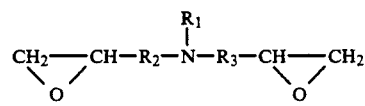

wherein
$R_1$ is alkyl having 1-20 carbon atoms, and
$R_2$ and $R_3$ each represent a hydrocarbon chain having 1-10 carbon atoms.

18. A particulate material comprising a plurality of porous mineral support particles impregnated with and containing a sufficient amount of an aminated polysaccharide polymer so as to permit reversibly fixing biologic macromolecules therewith, said support being a porous mineral oxide selected from the group consisting of silica, alumina, magnesia and an oxide of titanium, said aminated polysaccharide being affixed directly on the surface of said porous mineral support and said aminated polysaccharide being selected from the group consisting of (a) an aminated polysaccharide polymer having the formula

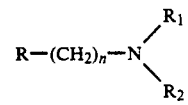

wherein
R is the residue of dextran, starch, cellulose or agarose,
n is a whole number from 1 to 10,
$R_1$ and $R_2$ each independently represent —CH₃, —CH₂—CH₃, —CH₂OH, —CH₂—CH₂OH or —CH₂—CHOH—CH₃, and (b) the aminated polysaccharide polymer of (a) quaternized with a quaternization agent selected from alkyl halide, hydroalkyl halide or dimethyl sulfate.

19. A process for preparing a particulate material comprising a plurality of porous mineral support particles impregnated with and containing a sufficient amount of an aminated polysaccharide polymer so as to permit reversibly fixing biologic macromolecules therewith,
said process comprising introducing into a chromatography column said porous mineral support particles, passing therethrough a buffer having a pH ranging from 3 to 12 until said column is equilibrated, introducing into said equilibrated column a solution of an aminated polysaccharide polymer in said buffer, said aminated polysaccharide being present in an amount (1) sufficient to impregnate said porous mineral support particles and (2) sufficient so that the resulting particulate material contains sufficient aminated polysaccharide so as to permit reversibly fixing biologic macromolecules therewith, whereby said aminated polysaccharide polymer is affixed directly on the surface of said porous mineral support particles, said porous mineral support particles being a porous mineral oxide selected from the group consisting of silica, alumina, magnesia and an oxide of titanium, and eluting the column with said buffer until an absence of aminated polysaccharide in the eluate is detected.

20. A process for preparing a particulate material comprising a plurality of porous mineral support particles impregnated with and containing a sufficient amount of an aminated polysaccharide polymer so as to permit reversibly fixing biologic macromolecules therewith, said process comprising impregnating said porous mineral support with an aqueous solution of an aminated polysaccharide polymer at a pH ranging from 3 to 2, said aminated polysaccharide being present in an amount sufficient so that the resulting particulate material contains sufficient aminated polysaccharide so as to permit reversibly fixing biologic macromolecules therewith, and whereby said aminated polysaccharide polymer is affixed directly on the surface of said porous mineral support, said porous mineral support being a porous mineral oxide selected from the group consisting of silica, alumina, magnesia and an oxide of titanium, and oven drying said impregnated support at a temperature ranging from 50° to 120° C. until a constant weight is achieved.

21. The process of claim 20 wherein the aminated polysaccharide polymer is present in said aqueous solution in an amount ranging from 1 to 10 weight percent thereof.

22. The process of claim 20 wherein said aminated polysaccharide polymer is present in said aqueous solution in an amount ranging from 5 to 8 weight percent thereof.

23. The process of claim 20 wherein the oven-dried impregnated support is treated with a solution of a crosslinking agent selected from 1,4-butanediol glycidyl ether or epichlorohydrin and is then dried at a temperature of about 40° to 120° C.

24. A use of a particulate material comprising a plurality of porous mineral support particles impregnated with and containing a sufficient amount of an aminated polysaccharide polymer so as to permit reversibly fixing biologic macromolecules therewith, said use comprising fixing therewith a macromolecular substance selected from antigens, antibodies or enzymes.

25. The use of claim 24 wherein said substance is irreversibly fixed by reticulation.

26. The use of claim 25 wherein said substance is tetanic anatoxin which is irreversibly fixed by reticulation with glutaraldehyde.

27. A use of a particulate material comprising a plurality of porous mineral support particles impregnated with and containing a sufficient amount of an aminated polysaccharide polymer so as to permit reversibly fixing biologic macromolecules therewith, said use comprising fixing therewith a low molecular weight substance selected from aminoacids, ligands, steroids or cellular receptors by coupling with a coupling agent selected from glutaraldehyde or a diepoxide of the formula 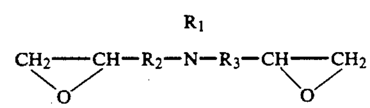 wherein $R_1$ is alkyl having 1 to 20 carbon atoms, and $R_2$ and $R_3$ each represent a hydrocarbon chain having 1 to 10 carbon atoms.

* * * * *